United States Patent [19]

Ichiki et al.

[11] 4,092,370
[45] May 30, 1978

[54] PROCESS FOR PRODUCING TETRACHLOROETHYLENE FROM TETRACHLOROMETHANE USING A MOLTEN SALT CATALYST

[75] Inventors: Eiichi Ichiki; Kazuo Iida; Satoshi Kamata; Yoshinori Kobayashi, all of Niihama, Japan

[73] Assignee: Sumitomo Chemical Company, Limited, Osaka, Japan

[21] Appl. No.: 620,009

[22] Filed: Sep. 30, 1975

Related U.S. Application Data

[63] Continuation of Ser. No. 289,039, Sept. 14, 1972, abandoned.

[30] Foreign Application Priority Data

Sep. 27, 1971  Japan .................................. 46-75577
Sep. 30, 1971  Japan .................................. 46-76872

[51] Int. Cl.$^2$ ..................... B01J 23/08; C07C 17/00; C07C 17/04; C07C 17/20
[52] U.S. Cl. .................... 260/658 R; 252/463; 252/467; 252/471; 252/474; 252/476; 260/654 A; 260/659 A; 260/660; 260/662A
[58] Field of Search ..................... 260/658 R, DIG. 42

[56] References Cited

U.S. PATENT DOCUMENTS

| | | | |
|---|---|---|---|
| 1,930,350 | 10/1933 | Strosacker et al. | 260/658 R X |
| 2,498,552 | 2/1950 | Kilgren et al. | 260/662 R |
| 2,727,076 | 12/1955 | Warren | 260/658 R |
| 2,890,250 | 6/1959 | Thermet et al. | 260/658 R |

FOREIGN PATENT DOCUMENTS

| | | | |
|---|---|---|---|
| 844,300 | 4/1939 | France | 260/658 R |
| 907,435 | 10/1962 | United Kingdom | 260/DIG. 42 |
| 1,213,402 | 11/1970 | United Kingdom | 260/654 A |

OTHER PUBLICATIONS

Krynitsky et al., J. Amer. Chem. Soc., vol. 71, pp. 816 to 819 (1949).
Bost et al., J. Amer. Chem. Soc., vol. 70, pp. 1027 to 1029 (1948).

*Primary Examiner*—Floyd D. Higel
*Attorney, Agent, or Firm*—Sughrue, Rothwell, Mion, Zinn and Macpeak

[57] ABSTRACT

Processes for producing tetrachloromethane and tetrachlorethylene are disclosed. Tetrachloromethane is produced by contacting a chlorinated feed material having two to four carbon atoms, and optionally including oxygen, hydrogen chloride or chlorine, with a molten salt catalyst of copper chloride together with an alkali metal or alkaline earth metal chloride at a temperature between 450° and 750° C. Tetrachloroethylene is produced by contacting tetrachloromethane, optionally together with chlorinatable material, oxygen and hydrogen chloride, with a similar catalyst at a temperature of 430° to 650° C.

9 Claims, No Drawings

PROCESS FOR PRODUCING TETRACHLOROETHYLENE FROM TETRACHLOROMETHANE USING A MOLTEN SALT CATALYST

This is a continuation of application Ser. No. 289,039, filed Sept. 14, 1972, now abandoned.

BACKGROUND OF THE INVENTION

1. Field of the Invention

This invention relates to a novel process for producing tetrachloroethylene or tetrachloromethane (carbon tetrachloride). More particularly, it relates to a process for producing tetrachloroethylene by a dechlorination dimerization of tetrachloromethane in the presence of a molten salt catalyst, and to a process for producing tetrachloromethane by the thermal chlorination decomposition of a completely chlorinated saturated and/or unsaturated hydrocarbon having from 2 to 4 carbon atoms in the presence of a molten salt catalyst.

2. Description of the Prior Art

It has heretofore been known to produce tetrachloroethylene from tetrachloromethane according to the following thermal equilibrium reaction:

$$2CCl_4 \rightleftarrows C_2Cl_4 + 2Cl_2$$

However, the rate of this reaction is extremely low and, for example, this reaction will not proceed at all at a temperature below 500° C. Accordingly, the production of tetrachloroethylene in accordance with this reaction on an industrial scale must be conducted at a temperature above about 550° C.

Also, it has hitherto been known to produce tetrachloromethane by the thermal chlorination decomposition reaction shown in the following equation wherein tetrachloroethylene is reacted with chlorine.

$$C_2Cl_4 + 2Cl_2 \rightleftarrows 2CCl_4$$

However, the rate of this reaction is also extremely low and, for example, this reaction will not proceed at a temperature below 500° C. Therefore, this reaction on an industrial scale must be conducted at a temperature of about 550° C. using a large excess of chlorine, e.g., in an amount of twice the theoretical amount.

If the reaction for converting tetrachloromethane to tetrachloroethylene or vice versa can be conducted at a lower temperature and at a higher reaction rate, it will be extremely valuable from an industrial viewpoint. However, such a process has not yet been established.

An object of the present invention is to provide a novel and economical process for producing tetrachloroethylene from tetrachloromethane.

Another object of the present invention is to provide a novel and economical process for producing tetracholomethane from a chlorinated hydrocarbon as a raw material.

SUMMARY OF THE INVENTION

As the result of extensive investigations on the process for producing tetrachloroethylene from tetrachloromethane or vice versa whose reaction rate is greater than that of above thermal equilibrium reaction or the thermal chlorination decomposition reaction, it was found that the production of tetrachloroethylene from tetrachloromethane can be conducted in accordance with the following reaction:

$$2CCl_4 + 4CuCl \rightarrow C_2Cl_4 + 4CuCl_2$$

at a reaction rate which is remarkably higher than that of the known thermal equilibrium reaction, and that tetrachloromethane can be produced from, for example, tetrachloroethylene in accordance with the following reaction:

$$C_2Cl_4 + 4CuCl_2 \rightarrow 2CCl_4 + 4CuCl$$

at a reaction rate which is remarkably higher than that of the known thermal chlorination decomposition reaction. Thus, the present invention has been completed on the basis of the above findings.

This invention provides a process for producing a chlorinated hydrocarbon which comprises contacting a feed material selected from the group consisting of (1) tetrachloromethane; (2) tetrachloromethane; and a chlorinatable material; (3) tetrachloromethane; a chlorinatable material; and oxygen; (4) tetrachloromethane; a chlorinatable material; oxygen; and hydrogen chloride, chlorine or a mixture of hydrogen chloride and chlorine; (5) a completely chlorinated saturated hydrocarbon having from 2 to 4 carbon atoms, a completely chlorinated unsaturated hydrocarbon having from 2 to 4 carbon atoms or mixtures of said saturated hydrocarbon and said unsaturated hydrocarbon; oxygen; and hydrogen chloride; and (6) a completely chlorinated saturated hydrocarbon having from 2 to 4 carbon atoms, a completely chlorinated unsaturated hydrocarbon having from 2 to 4 carbon atoms, or mixtures of said saturated hydrocarbon and said unsaturated hydrocarbon, and chlorine; with a molten salt catalyst at a temperature of from about 430° to 650° C. for feed material (1) to (4) and from about 430° to about 750° C. for feed materials (5) and (6), said molten salt catalyst comprising (A) a copper chloride (B) a mixture of a copper chloride and at least one chloride of an alkali metal or an alkaline earth metal; (C) a mixture of a copper chloride and at least one chloride of a second metal selected from the group consisting of iron, zinc, manganese, chromium, nickel, palladium and a rare earth metal or (D) a mixture of a copper chloride, at least one chloride of an alkali metal or an alkaline earth metal, and at least one chloride of a second metal selected from the group consisting of iron, zinc, manganese, chromium, nickel, palladium and a rare earth metal.

DETAILED DESCRIPTION OF THE INVENTION

In one embodiment of the process of the present invention, the invention comprises producing tetrachloroethylene by contacting tetrachloromethane; tetrachloromethane and a chlorinatable material; tetrachloromethane, a chlorinatable material and oxygen; or tetrachloromethane, a chlorinatable material, oxygen, hydrogen chloride and/or chlorine, with the above described molten salt catalyst at a temperature ranging from about 430° to about 650° C.

In another embodiment of the process of the present invention the invention comprises producing tetrachloromethane by contacting a chlorinated hydrocarbon feed, oxygen and hydrogen chloride; or a chlorinated hydrocarbon feed and chlorine, with the above described molten salt catalyst at a temperature ranging from about 430° to about 750° C.

The process for producing tetrachloroethylene from tetrachloromethane in accordance with one embodiment of the process of the present invention will be described in detail hereinunder.

As described above, the molten salt catalyst used in the invention comprises (A) a copper chloride (B) a mixture of a copper chloride and at least one chloride of an alkali metal and/or an alkaline earth metal, (C) a copper chloride and at least one chloride of a metal selected from the group consisting of iron, zinc, manganese, chromium, nickel, palladium and a rate earth metal or (D) a copper chloride, at least one chloride of an alkali metal or an alkaline earth metal and at least one chloride of a metal selected from the group consisting of iron, zinc, manganese, chromium, nickel, palladium and a rare earth metal. A catalyst system containing a chloride of a metal selected from the group consisting of iron, zinc, manganese, chromium, nickel, palladium and a rare earth metal is preferred. As used herein the term "copper chloride" includes both cuprous and cupric chloride.

The alkali metal chloride which can be used in the invention preferably includes lithium chloride, sodium chloride and potassium chloride and the alkaline earth metal chloride is preferably magnesium chloride.

These alkali metal or alkaline earth metal chlorides are mainly used to lower the melting point of the molten salt. Usually, the alkali metal chloride and/or the alkaline earth metal chloride is used as a mixture thereof in an amount of less than 3 moles, preferably, less than 2 moles per mole of the copper chloride.

Examples of the metal chlorides of (C) and (D) include iron chloride, zinc chloride, manganese chloride, palladium chloride, chromium chloride, nickel chloride, lanthanum chloride, cerium chloride, praseodymium chloride and neodymium chloride. These chlorides may be used either alone or as admixtures.

Particularly, in the system wherein a chlorinatable material is used, the molten salt catalyst containing the chlorides of a second metal selected from the group consisting of iron, zinc, manganese, palladium, chromium, nickel, and a rare earth metal i.e., catalysts (C) and (D), in which the total amount of these second metal chlorides is from 5 to 50 mole% is highly active and the molten salt catalyst of this type is particularly suitable for conducting the embodiment of the present invention. In addition, chlorides of silver, thalliium and the like may further be added to the molten salt catalyst of the invention.

The above-described molten salt of the invention is selected so that the salt or the mixture of the salt has a melting point of lower than 650° C.

The process of this invention for producing tetrachloroethylene from tetrachloromethane as described in this embodiment can effectively be carried out by contacting the molten salt catalyst with tetrachloromethane; tetrachloromethane and a chlorinatable material; tetrachloromethane, a chlorinatable material and oxygen; or tetrachloromethane, a chlorinatable material, oxygen, hydrogen chloride and/or chlorine.

A feed material in which a chlorinatable material is used is especially preferred because the chlorine liberated from the tetrachloromethane is rapidly removed by the chlorinatable material thereby increasing the conversion of tetrachloromethane to tetrachloroethylene.

In this embodiment, the process wherein tetrachloromethane and the chlorinatable material are used as feed materials is preferably employed where the chlorinatable material is mainly converted to an addition reaction product due to the chlorine liberated from tetrachloromethane, and the process wherein tetrachloromethane, the chlorinatable material and oxygen are used as feed materials is preferably employed where the chlorinatable material is mainly converted to a substitution reaction product. However, the invention is not limited to only these preferred embodiments.

Also, the use of tetrachloromethane, a chlorinatable material, oxygen, hydrogen chloride and/or chlorine as feed materials is by supplying tetrachloromethane to the reaction system of the chlorinatable material, oxygen, hydrogen chloride and/or chlorine, i.e., to the so-called oxychlorination reaction system. In this case, it is especially preferred to use tetrachloromethane produced by the oxychlorination reaction as a tetrachloromethane feed.

Tetrachloromethane used as a feed material in the embodiment of the present invention may be supplied either in a gaseous form or in a liquid form, and may be supplied together with other diluents.

The chlorinatable material used in the invention includes, for example, aliphatic hydrocarbons such as methane, ethane, propane, butane, ethylene, propylene, butene, butadiene, etc., a partially chlorinated derivative thereof, aromatic hydrocarbons such as benzene, toluene, xylene, etc. and the like. However, various other chlorinatable materials can also be employed.

Oxygen may be supplied as such or as a mixture of oxygen and an inert gas. Air is preferably used as oxygen source.

The only requirement for conducting the reaction of the invention is to use the above molten salt catalyst containing the copper chloride and to control the reaction temperature between about 430° and about 650° C. If the reaction temperature becomes lower than 430° C., the rate of the conversion of tetrachloromethane to tetrachloroethylene decreases, while if the reaction temperature exceeds 650° C., tetrachloromethane becomes tarry which results in a loss of the feed material. Thus, temperatures outside the above range are not preferred in the process of this invention.

Additionally, some of the molten salts used in the present invention are not in a molten state over the temperature range of from about 430° to about 650° C., i.e., some salts have a melting point of, for example, 500° C. In such case, the reaction is conducted at temperatures between 500° and 650° C., e.g. such that the catalyst is in a molten condition.

The proportion of the feed of tetrachloromethane, a chlorinatable material, oxygen, hydrogen chloride and/or chlorine varies depending upon the particular combination of the feed materials, the chlorinatable material, or the like. However, the proportion may easily be determined by preliminary experiments.

In carrying out this embodiment of the process of this invention, the reaction pressure is not critical, but, in general, the reaction can preferably be carried out under a pressure of from about 0 to about 30 Kg/cm$^2$ gauge pressure.

The residence time in the present invention somewhat varies depending upon the reaction condition, i.e., the reaction temperature, the molar ratio of feed materials, the molten salt and the chlorinatable material, etc.

However, in general, the residence time of from a fraction of a second to 60 seconds is sufficient.

The dechlorination dimerization of the tetrachloromethane feed and a chlorination reaction of the chlorinatable material can preferably be conducted by blowing the feed materials into the molten salt catalyst having the composition previously described or by passing the feed materials over the surface of the molten salt catalyst.

In preferred aspects for conducting the reaction of this embodiment, the starting tetrachloromethane, a chlorinatable material, oxygen, hydrogen chloride, chlorine, etc. are introduced into a reaction vessel to which the molten salt has been charged thereby effecting simultaneously the dechlorination dimerization reaction of tetrachloromethane and the chlorination reaction of the chlorinatable material. Alternatively, two separate reaction vessels are used for the dechlorination dimerization reaction of tetrachloromethane and for the reduction of the molten salt with a chlorinatable material, respectively, the molten salt charged in both of the reaction vessels being recycled between them, and tetrachloromethane and, if necessary, oxygen and a chlorine source are introduced into the former vessel and a chlorinatable material and, if necessary, oxygen and a chlorine source are introduced into the latter reaction vessel. However, the present invention is not limited to only these aspects.

The process for producing tetrachloromethane from a completely chlorinated saturated and/or unsaturated hydrocarbon having from 2 to 4 carbon atoms in accordance with a second embodiment of the present invention will be described in detail hereinafter.

The chlorinated hydrocarbon feed used in this embodiment of the invention includes tetrachloroethylene, hexachloroethane, octachloropropane, hexachlorobutadiene, octachlorobutene, decachlorobutane and mixtures thereof.

These chlorinated hydrocarbons may be used as a solution dissolved in a solvent such as tetrachloromethane, hexachloroethane, etc. Also, the feed material may, of course, be used as a mixture with an aliphatic hydrocarbon having from 1 to 4 carbon atoms or a partially chlorinated derivative thereof.

As described above, the molten salt catalyst in accordance with the present invention comprises (A) a copper chloride (B) a mixture of a copper chloride and at least one chloride of an alkali metal or an alkaline earth metal (C) a copper chloride and at least one chloride of a second metal selected from the group consisting of iron, zinc, manganese, chromium, nickel, palladium and a rare earth metal or (D) a copper chloride, at least one chloride of an alkali metal or an alkaline earth metal and at least one chloride of a second metal selected from the group consisting of iron, zinc, manganese, chromium, nickel, palladium and a rare earth metal. A catalyst system containing a chloride of a metal selected from the group consisting of iron, zinc, chromium, manganese, nickel, palladium and a rare earth metals is preferred, also. Also as used herein the term "copper chloride" including both cuprous chloride and cupric chloride.

The alkali metal chloride used in this embodiment of the invention also preferably includes lithium chloride, sodium chloride, potassium chloride, and the alkaline earth metal chloride is preferably magnesium chloride. These alkali metal chlorides and alkaline earth metal chlorides are mainly used in order to lower the melting point of the molten salt. Usually, the alkali metal chlorides and/or the alkaline earth metal chlorides are used as a mixture in an amount of less than 3 moles, preferably, less than 2 moles per mol of copper chloride.

Examples of the chlorides of (C) and (D) include iron chloride, zinc chloride, manganese chloride, chromium chloride, nickel chloride, palladium chloride, lanthanum chloride, cerium chloride, praseodymium chloride and neodymium chloride. These chlorides may be used either alone or as admixtures.

Especially, the molten salt catalyst containing the chlorides of a second metal selected from the group consisting or iron, zinc, manganese, palladium, chromium, nickel and a rare earth metal wherein the total amount of these second metal chlorides ranges from 5 to 50 mole% is highly active, and is preferably used also in the embodiment of the process of this invention. In addition, chlorides of silver, thallium and the like may further be added to the molten salt catalyst used in the present invention.

In carrying out this embodiment of the process of this invention, the molten salt catalyst is used within the temperature range of from about 430° to about 750° C., preferably, 500° to 650° C., with the catalyst being in a molten condition. If the temperature of the molten salt catalyst is below 430° C., the rate of the conversion of the chlorinated hydrocarbon feed to tetrachloromethane becomes low, while if the temperature of the molten salt catalyst exceeds 750° C., a cyclizing reaction of the chlorinated hydrocarbon feed occurs to produce hexachlorobenzene thereby resulting in a considerable loss of the chlorinated hydrocarbon feed. Thus, temperatures outside the above range are not preferred in the process of this invention.

Additionally, some of the molten salts used in the invention are not in a molten condition at a temperature ranging from about 430° to 750° C., i.e., some of the molten salts have a melting point of, for example, 500° C. In such a case, the reaction can be carried out at temperatures within the range of from 500° to about 750° C., i.e. such that the catalyst is molten.

In case where tetrachloroethylene, for instance, is used as the chlorinated feed material according to the present invention, the reaction proceeds as follows:

$$2CuCl_2 + C_2Cl_4 \rightarrow 2CuCl + C_2Cl_6 \tag{1}$$

$$2CuCl_2 + C_2Cl_6 \rightarrow 2CuCl + 2CCl_4 \tag{2}$$

Thus, tetrachloromethane is produced from tetrachloroethylene.

Cuprous chloride produced in the above reactions (1) and (2) can be converted to cupric chloride according to the following reaction by using hydrogen chloride and oxygen;

$$4CuCl + O_2 + 4HCl \rightarrow 4CuCl_2 + 2H_2O \tag{3}$$

or according to the following reaction by using chlorine;

$$4CuCl + 2Cl_2 \rightarrow 4CuCl_2 \tag{4}$$

In the oxychlorination reaction of this embodiment of the process of the present invention, substantially no combustion of the chlorinated hydrocarbon feed occurs since the chlorinated hydrocarbon feed reacts through the molten salt rather than reacting directly with the hydrogen chloride and oxygen. In addition, the conversion of the chlorinated hydrocarbon feed to tetrachloromethane is extremely high, and, further, the conversion of the chlorinated hydrocarbon feed to hexachlorobenzene is completely negligible.

Also, in the chlorination reaction of this embodiment of the present invention, the conversion of the chlorinated hydrocarbon feed to tetrachloromethane is extremely high and, in addition, the conversion of the chlorinated hydrocarbon feed to hexachlorobenzene is completely negligible, because the chlorinated hydrocarbon feed reacts through the molten salt rather than reacting directly with the chlorine.

In carrying out the process of this invention, the proportion of the starting chlorinated hydrocarbons, a source of chlorine and oxygen are not critical. That is, as can be understood from the above-described reactions (1) to (4), the reaction can be satisfactorily carried out under such conditions that cupric chloride is always present in the reaction system. In general, the chlorine source is used in an amount of from 0.1 to 20 moles (calculated as chlorine ($Cl_2$)) per mole of the chlorinated hydrocarbon feed, and, if hydrogen chloride is used as a chlorine source, oxygen is used in an amount of from 0.05 to 20 moles per mole of hydrogen chloride.

The oxygen can be used alone or in combination with an inert gas, preferably, air is used.

The chlorinated hydrocarbon feed may be supplied either in a gaseous form or a liquid form, and may be supplied as a mixture with other diluents. It is especially preferable to supply the chlorinated hydrocarbon feed together with an inert gas such as nitrogen, argon, helium and the like.

The conversion reaction of the chlorinated hydrocarbon feed to tetrachloromethane can be preferably carried out by blowing the chlorinated hydrocarbon feed and chlorine into the above described molten salt catalyst; or by blowing the chlorinated hydrocarbon feed, hydrogen chloride and oxygen into the molten salt catalyst, or by passing the reactants over the surface of the molten salt catalyst.

However, in the oxychlorination reaction, the chlorinated hydrocarbon feed, hydrogen chloride and oxygen are preferably supplied separately, or supplied as a mixture of the chlorinated hydrocarbon feed and hydrogen chloride or as a mixture of hydrogen chloride and oxygen, because a combustion reaction tends to occur if a mixture of chlorinated hydrocarbon feed and oxygen is supplied into the molten salt catalyst.

In preferred aspects for conducting the reaction of this embodiment, the chlorinated hydrocarbon feed, hydrogen chloride and oxygen, or the chlorinated hydrocarbon feed and chlorine are introduced into one reaction vessel, or two separate reaction vessels are used for the chlorination reaction of the chlorinated hydrocarbon feed and for the oxidation of the molten salt, respectively, the molten salt charged in both of the reaction vessels being recycled between them, and introducing the chlorinated hydrocarbon feed independently or in combination with hydrogen chloride into the former reaction vessel and introducing oxygen independently or in combination with hydrogen chloride into the latter vessel. However, the present invention is not restricted to only these aspects.

The residence time in this embodiment of the process of this invention somewhat varies depending upon the reaction conditions, i.e., reaction temperature, molar ratio of feed materials, the molten salt, etc. However, in general, the residence time of from a fraction of a second to 60 seconds is sufficient.

In carrying out this embodiment of the process of the present invention, the reaction pressure is not critical, but, in general, the reaction is conducted under a pressure of from about 0 to about 30 $Kg/cm^2$ gauge pressure.

The process of the invention described above in detail with reference to this embodiment makes it possible to produce tetrachloroethylene from tetrachloromethane with a reaction rate higher than that of the known process for the production of tetrachloroethylene from tetrachloromethane by the thermal equilibrium reaction. Accordingly, the process of the present invention is greatly advantageous from the industrial viewpoint.

Furthermore, the process of the invention also makes it possible in another embodiment of the process of this invention to produce tetrachloromethane in higher yield than that obtainable in the known process for the production of tetrachloromethane from an aliphatic hydrocarbon having 2 to 3 carbon atoms and/or a chlorinated hydrocarbon by the thermal chlorination decomposition reaction. In addition, the reaction rate of this embodiment of the process of this invention is extremely large as compared with known processes, i.e., the conventional process by the thermal chlorination decomposition reaction does not proceed at a temperature of 500° C, while the process of the present invention can be carried out at as low a temperature as about 430° C. Furthermore, at least a 100% excess amount of chlorine is required in the conventional thermal chlorination decomposition reaction, whereas in the process of the present invention, the reaction proceeds sufficiently as long as chlorine is used in an amount greater than the theoretical amount. Thus, the process of the present inventiion exhibits remarkable industrial advantages.

The process of the present invention will be illustrated in greater detail by reference to the following Examples and Comparative Examples, but these examples are not to be construed as limiting the present invention.

EXAMPLES 1-3

Into a quartz reaction tube of a 50 mm inside diameter and an 800 mm height equipped with a blowing inlet was charged 982 cc of the molten salt having the composition shown in Table 1, and maintained at the temperature indicated in Table 1. Thereafter, tetrachloromethane was introduced into the molten salt through the blowing inlet to effect the conversion reaction to tetrachloroethylene.

The reaction conditions and the results obtained are shown in Table 1 below.

Table 1

| | | Example No. | | |
|---|---|---|---|---|
| | | 1 | 2 | 3 |
| Reaction Conditions | Composition of the Molten Salt (mole %) | KCl 40 CuCl$_2$+ CuCl 60 | KCl 40 CuCl$_2$+ CuCl 60 | MnCl$_2$ 15 KCl 34 CuCl$_2$+ CuCl 51 |
| | Reaction Temperature (° C) | 450 | 550 | 520 |
| Feed Material | CCl$_4$ (mole/hr) | 0.542 | 0.618 | 0.740 |
| Product | Tetrachloroethylene (mole/hr) | 0.016 | 0.056 | 0.072 |
| | Hexachloroethane (mole/hr) | 0.009 | 0.003 | 0.007 |

Table 1-continued

|  | Example No. | | |
|---|---|---|---|
|  | 1 | 2 | 3 |
| Others | Trace | Trace | Trace |
| Conversion of $CCl_4$ to $C_2Cl_4$ (%) | 6 | 18 | 19 | ylene was introduced into the molten salt together with nitrogen in a gaseous form through one blowing inlet, and hydrogen chloride and air were introduced into the molten salt through the other blowing inlet to effect the oxychlorination reaction of tetrachloroethylene continuously for 1 hour.

The reaction conditions and the results obtained are shown in Table 3.

Table 3

|  |  | Example No. | | | |
|---|---|---|---|---|---|
|  |  | 7 | 8 | 9 | 10 |
| Reaction Conditions | Composition of the Molten Salt (mole %) | KCl 40<br>$CuCl_2+$<br>$CuCl$ 60 | KCl 40<br>$CuCl_2+$<br>$CuCl$ 60 | $FeCl_3$ 10<br>KCl 36<br>$CuCl_2+$<br>$CuCl$ 54 | $FeCl_3$ 8<br>$PdCl_2$ 7<br>KCl 25.5<br>$CuCl_2+$<br>$CuCl$ 59.5 |
|  | Reaction Temperature (° C) | 450 | 550 | 550 | 550 |
| Feed Material | $C_2Cl_4$ (mole/hr) | 0.291 | 0.258 | 0.223 | 0.287 |
|  | HCl (liter/hr) | 24 | 24 | 24 | 24 |
|  | Air (liter/hr) | 30 | 30 | 30 | 30 |
| Reaction Product | $CCl_4$ (mole/hr) | 0.012 | 0.077 | 0.086 | 0.137 |
|  | Hexachloroethane (mole/hr) | 0.009 | 0.007 | 0.031 | 0.032 |
|  | CO, $CO_2$ (mole/hr) | 0.001 | 0.002 | Trace | Trace |
|  | Others | Trace | Trace | Trace | Trace |
| Conversion (%) of $C_2Cl_4$ to $CCl_4$ |  | 2 | 15 | 19 | 24 |

EXAMPLES 4-6

Into a quartz reaction tube of a 50 mm inside diameter and a 400 mm height equipped with a blowing inlet was charged 295 cc of the molten salt having the composition shown in Table 2, and maintained at the temperature shown in Table 2. Thereafter, tetrachloromethane and methane were introduced into the molten salt through the blowing inlet to effect the conversion reaction to tetrachloroethylene. The reaction conditions and the results obtained are shown in Table 2 below.

Table 2

|  |  | Example No. | | |
|---|---|---|---|---|
|  |  | 4 | 5 | 6 |
| Reaction Conditions | Composition of the Molten Salt (mole %) | KCl 40<br>$CuCl_2+$<br>$CuCl$ 60 | $FeCl_3$ 10<br>KCl 36<br>$CuCl_2+$<br>$CuCl$ 54 | $NdCl_3$ 5<br>$MnCl_2$ 10<br>KCl 34<br>$CuCl_2+$<br>$CuCl$ 51 |
|  | Reaction Temperature (° C) | 520 | 520 | 510 |
| Feed Material | $CCl_4$ (mole/hr) | 0.788 | 0.787 | 0.790 |
|  | $CH_4$ (mole/hr) | 0.268 | 0.268 | 0.268 |
| Product | $CH_2Cl_2$ (mole/hr) | 0.008 | Trace | Trace |
|  | $CHCl_3$ (mole/hr) | 0.040 | 0.005 | 0.003 |
|  | $CCl_4$ (mole/hr) | 0.503 | 0.634 | 0.618 |
|  | $C_2HCl_3$ (mole/hr) | 0.001 | Trace | Trace |
|  | $C_2Cl_4$ (mole/hr) | 0.175 | 0.193 | 0.213 |
|  | $C_2Cl_6$ (mole/hr) | 0.019 | 0.012 | 0.004 |
|  | Others | Trace | Trace | Trace |
| Conversion of $CH_4$ (%) |  | 57 | 98 | 99 |
| Conversion of $CCl_4$ Charged* (%) |  | 36 | 19 | 22 |

*values determined by calculating the total $CCl_4$ in the reaction product as unreacted charged $CCl_4$.

EXAMPLES 7-10

Into a quartz reaction tube of a 50 mm inside diameter and an 800 mm height equipped with two blowing inlets was charged 982 cc of the molten salt having the composition shown in Table 3, and maintained at the temperature shown in Table 3. Thereafter, tetrachloroeth-

EXAMPLES 11-13

An oxychlorination reaction of hexachlorobutadiene was carried out in the same manner as in Example 7. The reaction conditions and the results obtained are shown in Table 4.

Table 4

|  |  | Example No. | | |
|---|---|---|---|---|
|  |  | 11 | 12 | 13 |
| Reaction Conditions | Composition of the Molten Salt (mole %) | $MnCl_2$ 15<br>KCl 42.5<br>$CuCl_2+$<br>$CuCl$ 42.5 | $MnCl_2$ 10<br>$LaCl_3$ 5<br>KCl 42.5<br>$CuCl_2+$<br>$CuCl$ 42.5 | $PdCl_2$ 7<br>$MnCl_2$ 8<br>KCl 42.5<br>$CuCl_2+$<br>$CuCl$ 42.5 |
|  | Reaction Temperature (° C) | 600 | 650 | 700 |
| Feed material | $C_4Cl_6$ (mole/hr) | 0.140 | 0.193 | 0.201 |
|  | HCl (liter/hr) | 30 | 30 | 30 |
|  | Air (liter/hr) | 38 | 38 | 38 |
| Reaction Product | $CCl_4$ (mole/hr) | 0.010 | 0.079 | 0.159 |
|  | Tetrachloroethylene (") | 0.002 | 0.013 | 0.021 |
|  | Hexachloroethane (") | 0.002 | 0.011 | 0.011 |
|  | CO, $CO_x$ (") | Trace | Trace | Trace |
|  | Others (") | Trace | 0.003 | 0.004 |
| Conversion (%) of $C_4Cl_6$ to $CCl_4$ |  | 2 | 10 | 20 |

EXAMPLES 14-16

An oxychlorination reaction of octachlorobutene was conducted in the same manner in Example 7. The reaction conditions and the results obtained are shown in Table 5.

Table 5

|  |  | Example No. | | |
|---|---|---|---|---|
|  |  | 14 | 15 | 16 |
| Reaction | Composition of |  $NiCl_2$ 5 | $MgCl_2$ 5 | $CrCl_3$ 10 |

Table 5-continued

| Conditions | | Example No. 14 | Example No. 15 | Example No. 16 |
|---|---|---|---|---|
| Conditions | the Molten Salt (mole %) | $ZnCl_2$ 15 $KCl$ 32 $CuCl_2$+ $CuCl$ 48 | $ZnCl_2$ 38 $CuCl_2$+ $CuCl$ 57 | $NdCl_3$ 10 $KCl$ 32 $CuCl_2$+ $CuCl$ 48 |
| | Reaction Temperature (° C) | 580 | 550 | 550 |
| Feed Material | $C_4Cl_8$ (mole/hr) | 0.185 | 0.134 | 0.209 |
| | HCl (liter/hr) | 24 | 24 | 24 |
| | Air (liter/hr) | 30 | 30 | 30 |
| Reaction Product | $CCl_4$ (mole/hr) | 0.148 | 0.114 | 0.250 |
| | Tetrachloroethylene (″) | 0.203 | 0.144 | 0.211 |
| | Hexachloroethane (″) | 0.092 | 0.066 | 0.081 |
| | CO, $CO_2$ (″) Others (″) | Trace ″ | Trace ″ | Trace ″ |
| Conversion (%) of $C_4Cl_8$ to $CCl_4$ | | 20 | 21 | 30 |

While the invention has been described in detail and with reference to specific embodiments thereof, it will be apparent that various changes can be made therein without departing from the spirit and scope thereof.

What is claimed is:

1. A process for producing tetrachloroethylene which comprises contacting a feed material selected from the group consisting of (1) tetrachloromethane; (2) tetrachloromethane; and a chlorinatable material; (3) tetrachloromethane; a chlorinatable material; and oxygen and (4) tetrachloromethane; a chlorinatable material; oxygen; and hydrogen chloride, chlorine, or a mixture of hydrogen chloride and chlorine; at a temperature of from about 430° C to 650° C with a salt catalyst which is molten at the reaction temperature, said molten salt catalyst consisting essentially of a mixture of a copper chloride and at least one chloride of an alkali metal or an alkaline earth metal, and recovering the tetrachloroethylene.

2. The process of claim 1, wherein said molten salt catalyst additionally includes at least one chloride of an alkali metal or an alkaline earth metal, and at least one chloride of a second metal selected from the group consisting of iron, zinc, manganese, chromium, nickel, palladium and a rare earth metal.

3. The process of claim 2, wherein the amount of said chloride of said second metal in said molten salt catalyst is from 5 to 50 mole %.

4. The process of claim 2, wherein said alkali metal chloride, alkaline earth metal chloride or mixture thereof is present in said molten salt catalyst in an amount of less than 3 moles per mole of said copper chloride.

5. The process of claim 2, wherein said amount is less than 2 moles per mole of said copper chloride.

6. The process of claim 2, wherein said oxygen is air.

7. The process of claim 2, wherein said alkali metal chloride is lithium chloride, sodium chloride or potassium chloride.

8. The process of claim 2, wherein said alkaline earth metal chloride is magnesium chloride.

9. The process of claim 2, wherein said molten salt catalyst additionally contains silver chloride or thallium.

* * * * *